US00PP35633P2

(12) United States Plant Patent
Nelson

(10) Patent No.: US PP35,633 P2
(45) Date of Patent: Feb. 6, 2024

(54) COLORADO BLUE SPRUCE TREE NAMED 'WARDS BLUE WAVES'

(50) Latin Name: ***Picea pungens* var. *glauca***
Varietal Denomination: Wards Blue Waves

(71) Applicant: Randall S. Nelson, Forest Grove, OR (US)

(72) Inventor: Randall S. Nelson, Forest Grove, OR (US)

(73) Assignee: TREESAP FARMS LLC, Houston, TX (US)

( * ) Notice: Subject to any disclaimer, the term of this patent is extended or adjusted under 35 U.S.C. 154(b) by 0 days.

(21) Appl. No.: 18/205,004

(22) Filed: Jun. 2, 2023

(51) Int. Cl.
*A01H 7/00* (2006.01)
*A01H 6/00* (2018.01)

(52) U.S. Cl.
USPC ..... Plt./213
CPC ..... *A01H 6/00* (2018.05)

(58) Field of Classification Search
USPC ..... Plt./213
CPC ..... A01H 7/00
See application file for complete search history.

*Primary Examiner* — Kent L Bell
(74) *Attorney, Agent, or Firm* — Penny J. Aguirre

(57) ABSTRACT

A new cultivar of Colorado blue spruce tree named 'Wards Blue Waves' characterized by its foliage that is silvery blue in appearance in color year around, its foliage with a very glaucous surface, its branch apexes that curve upwards, its dense and compact plant habit, its conical shape, and its short plant height; reaches 6 m after 20 years when grown in Oregon.

2 Drawing Sheets

Botanical classification: *Picea pungens* var. *glauca*.
Varietal denomination: 'Wards Blue Waves'.

This application is related to a U.S. Plant Patent Application filed for a plant derived from the same Inventor that is entitled Colorado Blue Spruce Tree Named 'Hymes Blue Dream' (U.S. Plant patent application Ser. No. 18/205,003).

BACKGROUND OF THE INVENTION

The present invention relates to a new and distinct cultivar of *Picea pungens* var. *glauca* and will be referred to hereafter by its cultivar name, 'Wards Blue Waves'. 'Wards Blue Waves' represents a new cultivar of Colorado blue spruce, an evergreen plant grown for landscape use.

The inventor discovered 'Wards Blue Waves' as a chance seedling in October of 2001 that was growing in a production field planted with unnamed plants of *Picea pungens* var. *glauca* at his nursery in Forest Grove, Oregon. The parent plants are therefore unknown.

Asexual propagation of the new cultivar was first accomplished by grafting in Forest Grove, Oregon in winter of 2002 under the direction of the Inventor. Asexual propagation by grafting has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Wards Blue Waves' as a unique cultivar of *Picea*.

1. 'Wards Blue Waves' exhibits foliage that is silvery blue in appearance in color year around.
2. 'Wards Blue Waves' exhibits foliage with a very glaucous surface.
3. 'Wards Blue Waves' exhibits branch apexes that curve upwards.

4. 'Wards Blue Waves' exhibits a dense and compact plant habit.
5. 'Wards Blue Waves' exhibits a conical shape.
6. 'Wards Blue Waves' exhibits a short plant height; reaches 6 m after 20 years when grown in Oregon.

The unnamed plants of *Picea pungens* var. *glauca* growing in the area of discovery differ from 'Wards Blue Waves' in having more open and upright growth habits, foliage that is dark green to dark gray color foliage, less compact plant habits, longer stem internodes, and in being taller in height. 'Wards Blue Waves' can be most closely compared to *Picea pungens* var. *glauca* cultivars 'Apache' (not patented) and 'Hymes Blue Dream'. 'Apache' differs from 'Wards Blue Waves' in having less glaucous foliage, longer internodes, and a taller plant height. 'Hymes Blue Dream' differs from 'Wards Blue Waves' in having foliage that is less silvery blue in winter and lacking the branch apices that are curved upwards.

BRIEF DESCRIPTION OF THE DRAWINGS

The accompanying color photographs illustrate the overall appearance and distinct characteristics of the new *Picea*. The photographs were taken of 21-year-old trees as grown in the ground in Forest Grove, Oregon.

Figure 1:
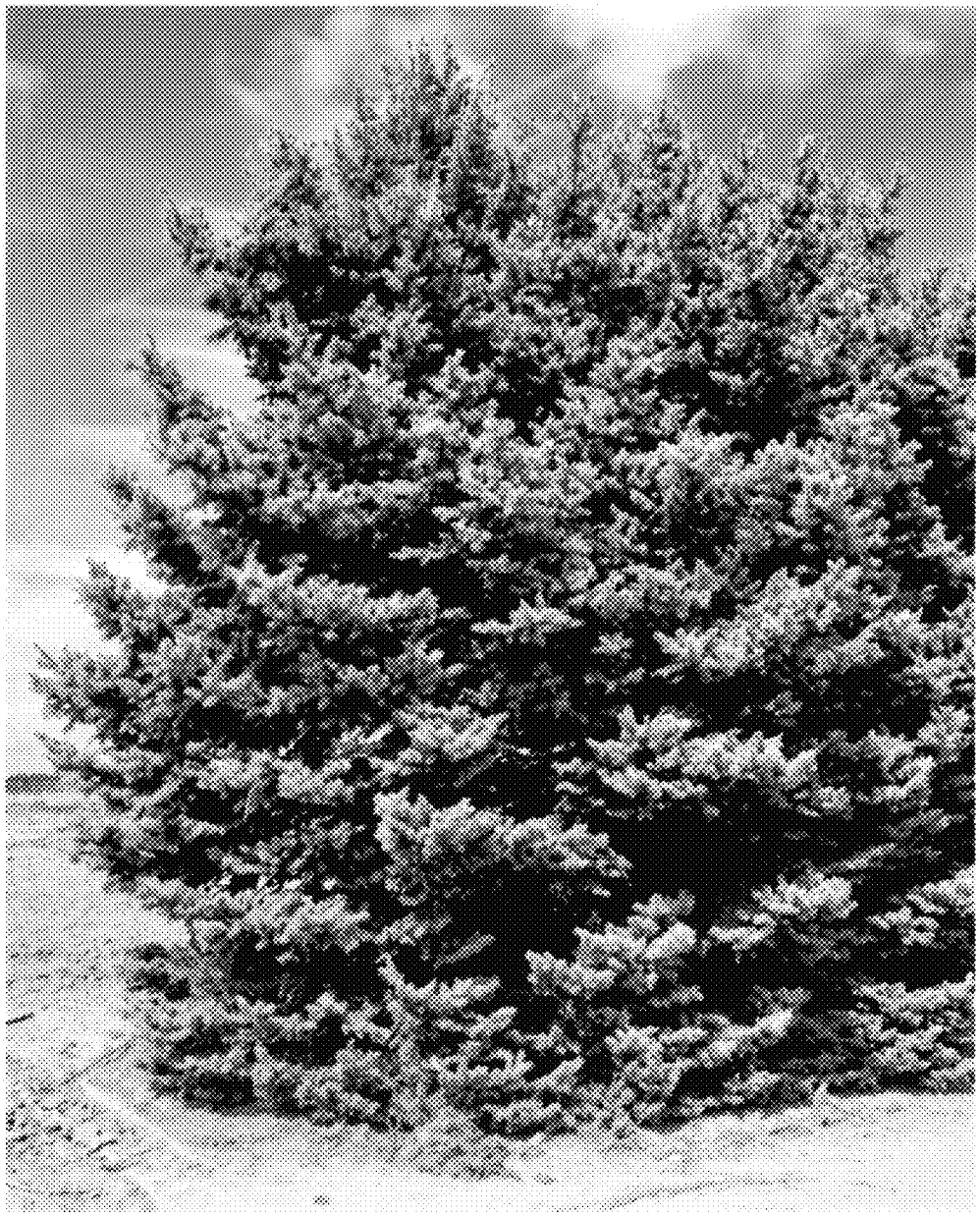
FIG. 1 provides an overall view of the plant habit of 'Wards Blue Waves'.
Figure 2:
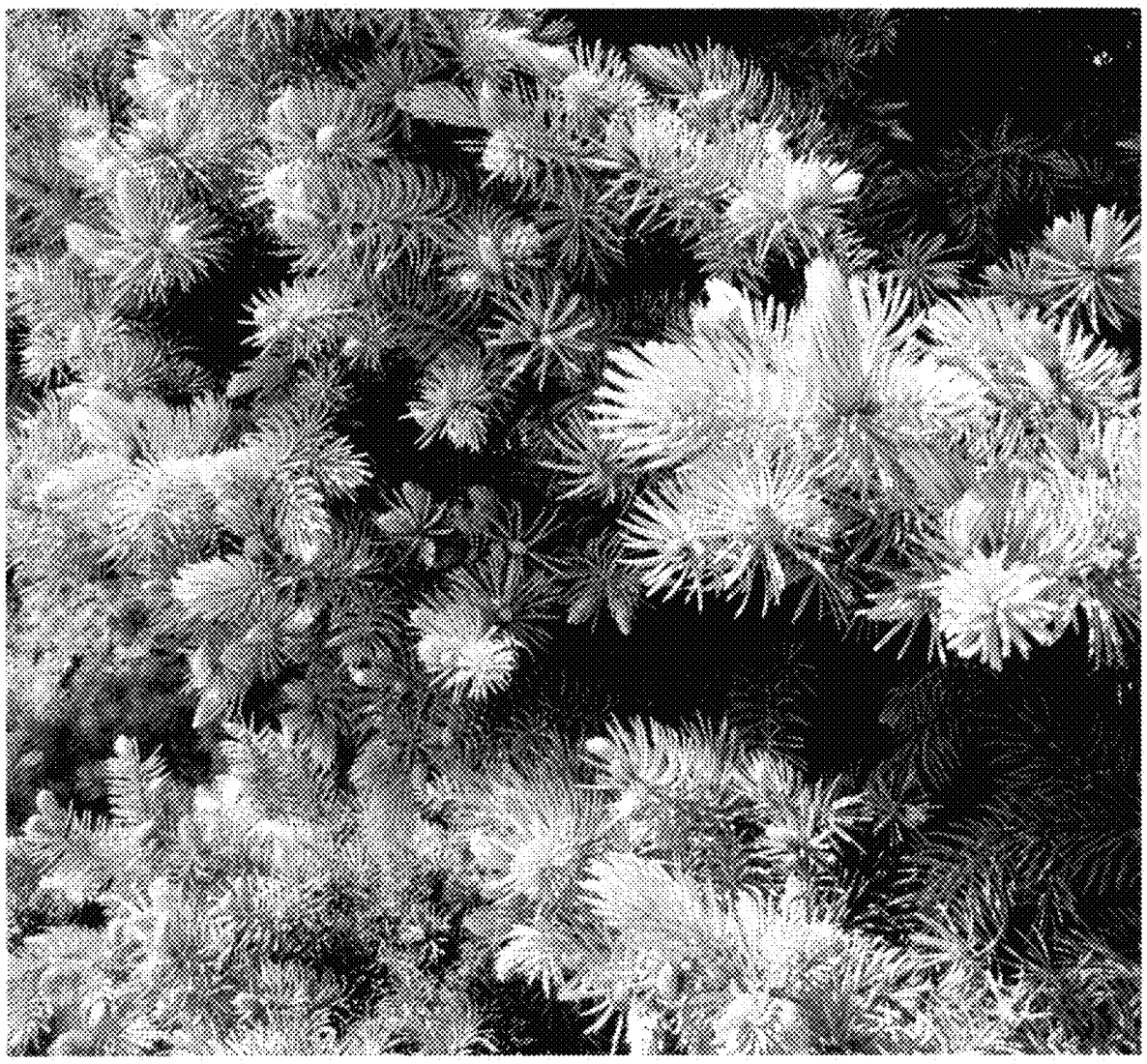
FIG. 2 provides a close-up view of the foliage of 'Wards Blue Waves'.

The colors in the photographs are as close as possible with the photographic and printing technology utilized. The color values cited in the detailed botanical description accurately describe the colors of the new *Picea*.

DETAILED BOTANICAL DESCRIPTION

The following is a detailed description of the new cultivar as taken from 2-year-old trees grown in 1-gallon nursery containers in Forest Grove, Oregon. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Plant type.*—Coniferous evergreen.

*Growth habit.*—Conical, dense, upright.

*Height and spread.*—An average of 35 cm in height and 20 cm in width as grown in a one-gallon container, reaches 5.5 m in height and 2.5 m in width in 10 years, a 20 -year-old tree will reach 6 m in height in the landscape.

*Cold hardiness.*—At least in U.S.D.A. Zone 3.

*Diseases and pests.*—No susceptibility or resistance to pests or diseases has been observed.

*Root description.*—Fibrous, moderately branched, moderately thick, a blend of N199B and N199C in color.

*Growth rate.*—Moderate, 10 to 15 cm of new growth in spring.

*Propagation.*—Grafting.

*Root development.*—Grafted in late winter with final scion successfully grafted in approximately 20 weeks, time required to produce a young tree; 12 months.

Branch description:

*Trunk and branch shape.*—Rounded.

*Branch size.*—Main trunk; 22 cm in length, 1.5 cm in diameter, lateral branches; average of 14.5 cm in length, up to 3 cm in width, tertiary branches; up to 5 cm in length, 3 mm in width.

*Stem surface.*—Young stems; smooth, matte, linear streaks cover the surface, mature and old wood; rugose, bark-like and matte.

*Branching.*—Average of 14 lateral branches, 4 tertiary branches per lateral, strong central leader.

*Stem arrangement.*—Lateral branches; whorled to opposite, tertiary branches; opposite.

*Stem aspect.*—Strong, main stem vertical, lateral and tertiary stems held in a slightly upright angle, apex of new branches curved upwards.

*Internode length.*—1 to 5 cm.

*Stem color.*—Young stems; striations of 164A and 164B, mature stems; close to 164B, old wood; blend of N200D and 199B.

*Resin glands.*—None observed.

Foliage description:

*Leaf arrangement.*—Densely whorled needles.

*Leaf attachment.*—Sessile.

*Leaf shape.*—Acicular, needle shaped.

*Leaf division.*—Simple.

*Leaf base.*—Cuneate.

*Leaf apex.*—Sharp and pointed, linear.

*Leaf venation.*—Not visible.

*Leaf margins.*—Entire.

*Leaf fragrance.*—When crushed, it produces a pine-like fragrance.

*Leaf surface.*—Upper and lower surface; matte, highly glaucous.

*Leaf color.*—Emerging; 138B, year around with sun exposure 190A with heavy glaucous coating of 97D, shaded foliage 138B.

*Leaf texture.*—Dense, stiff and strong.

*Leaf aspect.*—Vertical to slightly bowed to branch.

*Leaf size.*—An average of 2.3 cm in length and 1.5 mm in diameter.

*Leaf quantity.*—Average of 150 per branch 11 cm in length.

*Leaf buds.*—Average cluster of 3 on a lateral branch, up to 5 mm in length and 3 mm in width, 172A in color, comprised of imbricate scales orbicular and cupped in shape and average of 1 mm in length and width.

Cone description: Cone production has not been observed to date.

It is claimed:

1. A new and distinct cultivar of Colorado Blue Spruce tree named 'Wards Blue Waves' as herein illustrated and described.

* * * * *